(12) United States Patent
McAuley et al.

(10) Patent No.: US 9,539,404 B2
(45) Date of Patent: *Jan. 10, 2017

(54) BREATHING ASSISTANCE APPARATUS (71) Applicant: Fisher & Paykel Healthcare Limited, Auckland (NZ)

(72) Inventors: Alastair Edwin McAuley, Auckland (NZ); Ivan Milivojevic, London (GB)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 14/840,497

(22) Filed: Aug. 31, 2015

(65) Prior Publication Data

US 2016/0051786 A1 Feb. 25, 2016

Related U.S. Application Data (63) Continuation of application No. 10/582,447, filed as application No. PCT/NZ2004/000315 on Dec. 6, 2004, now Pat. No. 9,119,929.

(30) Foreign Application Priority Data

Dec. 8, 2003 (NZ) ........................................ 530060

(51) Int. Cl.
*A61M 16/06* (2006.01)
(52) U.S. Cl.
CPC ......... *A61M 16/0622* (2014.02); *A61M 16/06* (2013.01); *A61M 16/0616* (2014.02); *A61M 16/0688* (2014.02); A61M 2016/0661 (2013.01)

(58) Field of Classification Search
CPC ...... A61M 16/06–16/0655; A61M 2016/0661; A62B 7/00–7/04; A62B 7/14; A62B 18/00; A62B 18/02–18/04
See application file for complete search history.

(56) References Cited

U.S. PATENT DOCUMENTS

| | | |
|---|---|---|
| 2,228,218 A | 1/1941 | Schwartz |
| 2,939,458 A | 6/1960 | Lundquist |
| 4,938,209 A | 7/1990 | Fry |
| 5,031,261 A | 7/1991 | Fenner |
| 5,243,971 A | 9/1993 | Sullivan et al. |
| 5,441,046 A | 8/1995 | Starr et al. |
| 5,449,206 A | 9/1995 | Lockwood |
| 5,518,802 A | 5/1996 | Colvin et al. |
| 5,570,689 A | 11/1996 | Starr et al. |
| 5,857,460 A | 1/1999 | Popitz |

(Continued)

FOREIGN PATENT DOCUMENTS

| | | |
|---|---|---|
| AU | 2003246441 | 12/2003 |
| EP | 0 427 474 | 11/1990 |

(Continued)

OTHER PUBLICATIONS

Supplementary Partial European Search Report, Mar. 1, 2011, 6 pages.

*Primary Examiner* — Rachel Young
(74) *Attorney, Agent, or Firm* — Knobbe, Martens, Olson & Bear LLP.

(57) ABSTRACT

A mask with cushion that has an outer film is disclosed. The film may be self-skinning or a film formed about or glued to the cushion body. In another form the cushion may be formed with at least a portion having a plurality of adjacent voids having honeycomb-like structure.

16 Claims, 8 Drawing Sheets

(56) References Cited

U.S. PATENT DOCUMENTS

| | | |
|---|---|---|
| 5,884,624 A | 3/1999 | Barnett et al. |
| 6,016,804 A | 1/2000 | Gleason et al. |
| 6,039,044 A | 3/2000 | Sullivan |
| 6,112,746 A | 9/2000 | Kwok et al. |
| 6,116,235 A | 9/2000 | Walters et al. |
| 6,347,631 B1 | 2/2002 | Hansen et al. |
| 6,467,483 B1 | 10/2002 | Kopacko et al. |
| 6,513,526 B2 | 2/2003 | Kwok et al. |
| 6,581,602 B2 | 6/2003 | Kwok et al. |
| 6,615,832 B1 | 9/2003 | Chen |
| 6,631,718 B1 | 10/2003 | Lovell |
| 6,634,358 B2 | 10/2003 | Kwok et al. |
| 6,736,139 B1 | 5/2004 | Wix |
| 6,883,177 B1 | 4/2005 | Ouellette et al. |
| 6,895,965 B2 | 5/2005 | Scarberry et al. |
| 6,907,882 B2 | 6/2005 | Ging et al. |
| 7,007,696 B2 | 3/2006 | Palkon et al. |
| 7,021,311 B2 | 4/2006 | Gunaratnam et al. |
| 7,077,126 B2 | 7/2006 | Kummer et al. |
| 7,290,546 B2 | 11/2007 | Sprinkle et al. |
| 7,353,827 B2 | 4/2008 | Geist |
| 7,523,754 B2 | 4/2009 | Lithgow et al. |
| 7,665,464 B2 | 2/2010 | Kopacko et al. |
| 7,681,575 B2 | 3/2010 | Wixey et al. |
| 8,479,726 B2 | 7/2013 | McAuley |
| 8,567,404 B2 | 10/2013 | Davidson et al. |
| 9,072,852 B2 | 7/2015 | McAuley et al. |
| 9,119,929 B2 | 9/2015 | McAuley et al. |
| 9,295,799 B2 | 3/2016 | McAuley et al. |
| 2001/0020474 A1 | 9/2001 | Hecker et al. |
| 2002/0014241 A1 | 2/2002 | Gradon et al. |
| 2002/0026934 A1 | 3/2002 | Lithgow et al. |
| 2002/0100479 A1 | 8/2002 | Scarberry et al. |
| 2003/0019495 A1 | 1/2003 | Palkon et al. |
| 2003/0019496 A1 | 1/2003 | Kopacko et al. |
| 2003/0089373 A1 | 5/2003 | Gradon et al. |
| 2003/0149384 A1 | 8/2003 | Davis et al. |
| 2003/0196658 A1 | 10/2003 | Ging et al. |
| 2003/0217746 A1 | 11/2003 | Gradon et al. |
| 2004/0035427 A1 | 2/2004 | Bordewick et al. |
| 2004/0118412 A1 | 6/2004 | Piletti-Reyes |
| 2004/0182398 A1 | 9/2004 | Sprinkle et al. |
| 2005/0199239 A1 | 9/2005 | Lang et al. |
| 2006/0096598 A1 | 5/2006 | Ho et al. |
| 2006/0254593 A1 | 11/2006 | Chang |
| 2007/0221227 A1 | 9/2007 | Ho |
| 2007/0267017 A1 | 11/2007 | McAuley et al. |
| 2008/0110464 A1 | 5/2008 | Davidson et al. |
| 2009/0044808 A1 | 2/2009 | Guney et al. |
| 2015/0090266 A1 | 4/2015 | Melidis et al. |
| 2016/0001028 A1 | 1/2016 | McAuley et al. |
| 2016/0051786 A1 | 2/2016 | McaAuley et al. |
| 2016/0213873 A1 | 7/2016 | McAuley et al. |

FOREIGN PATENT DOCUMENTS

| | | |
|---|---|---|
| EP | 0 427 474 | 5/1991 |
| EP | 1 099 452 | 5/2001 |
| EP | 1 258 266 | 11/2002 |
| WO | WO 82/03548 | 10/1982 |
| WO | WO 98/04310 | 2/1998 |
| WO | WO 98/24499 | 6/1998 |
| WO | WO 98/48878 | 11/1998 |
| WO | WO 99/58198 | 11/1999 |
| WO | WO 00/78384 | 12/2000 |
| WO | WO 01/97893 | 12/2001 |
| WO | WO 02/11804 | 2/2002 |
| WO | WO 03/092755 | 11/2003 |
| WO | WO 2004/007010 | 1/2004 |
| WO | WO 2004/030736 | 4/2004 |
| WO | WO 2005/018523 | 3/2005 |
| WO | WO 2006/074513 | 7/2006 |
| WO | WO 2006/074514 | 7/2006 |
| WO | WO 2007/009182 | 1/2007 |

BREATHING ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation application of U.S. application Ser. No. 10/582,447, filed May 18, 2007, which is a national phase filing of PCT Application No. PCT/NZ2004/00315, filed Dec. 6, 2004, which claims a priority benefit to New Zealand Patent Application No. 530060, filed Dec. 8, 2003.

BACKGROUND OF THE INVENTION

Field of the Invention

This invention relates to patient interfaces particularly though not solely for use in delivering CP AP therapy to patients suffering from obstructive sleep apnoea (OSA). In particular, this invention relates to cushions used to support and seal the mask to a patient's face.

Description of the Related Art

In the art of respiration devices, there are well known variety of respiratory masks which cover the nose and/or mouth of a human patient in order to provide a continuous seal around the nasal and/or oral areas of the face such that gas may be provided at positive pressure within the mask for consumption by the patient. The uses for such masks range from high altitude breathing (i.e., aviation applications) to mining and fire fighting applications, to various medical diagnostic and therapeutic applications.

One requisite of such respiratory masks has been that they provide an effective seal against the patient's face to prevent leakage of the gas being supplied. Commonly, in prior mask configurations, a good mask-to-face seal has been attained in many instances only with considerable discomfort for the patient. This problem is most crucial in those applications, especially medical applications, which require the patient to wear such a mask continuously for hours or perhaps even days. In such situations, the patient will not tolerate the mask for long durations and optimum therapeutic or diagnostic objectives thus will not be achieved, or will be achieved with great difficulty and considerable patient discomfort.

U.S. Pat. No. 5,243,971 and U.S. Pat. No. 6,112,746 are examples of prior art attempts to improve the mask system U.S. Pat. No. 5,570,689 and PCT publication No. WO 00/78384 are examples of attempts to improve the forehead rest.

U.S. Pat. No. 6,634,358 and U.S. Pat. No. 6,581,602 of ResMed Limited disclose a nasal mask cushion to sealingly connect a mask to a wearer's face. The cushion has a nose-receiving cavity bounded by a frame and membrane. The membrane is spaced away from the rim of the frame, and its outer surface is of substantially the same shape as the rim.

In the prior art mask cushions are provided that have a solid inner wall that provides support but doesn't allow much change in the shape of the cushion. Thus, such mask cushions can be uncomfortable for a user. Furthermore, often prior art mask cushions are made of foam which is neither waterproof nor durable.

SUMMARY OF THE INVENTION

It is an object of the present invention to attempt to provide a patient interface which goes some way to overcoming the abovementioned disadvantages in the prior art or which will at least provide the industry with a useful choice.

Accordingly in a first aspect the present invention consists in a cushion for a patient interface adapted to supply gas to a patient comprising:
   a cushion body; and
   an outer cover,
   wherein said body and cover are substantially formed of the same elemental material.

Preferably said elemental material is polyurethane.

Preferably said cushion body is formed in polyurethane foam.

Preferably said outer cover is formed in polyurethane film.

Preferably said outer cover is adhered to said body.

Preferably said cushion body is assembled from more than one moulded component.

Preferably said cushion body includes an attachment adapted to engage a mask.

In a second aspect the present invention consists in a cushion for a patient interface adapted to supply gas to a patient comprising:
   a cushion body having an outer cover, and
   an outer sealing sheath,
   wherein said cushion body is detachable from said outer sheath and said patient interface.

Preferably said cushion body and said outer sealing sheath are formed of the same elemental material.

Preferably said elemental material is silicone.

In a third aspect the present invention consists in a mask adapted to deliver gas to a patient comprising:
   a cushion body wherein at least a portion thereof has a plurality of adjacent voids.

Preferably each of said voids has a hexagonal cross section.

Preferably each of said voids has an oval, square, rectangular, or other shaped cross section.

Preferably said cushion body has an outer cover and said mask further includes an outer sealing sheath.

BRIEF DESCRIPTION OF THE DRAWINGS

Preferred forms of the present invention will now be described with reference to the accompanying drawings.

DETAILED DESCRIPTION OF THE PREFERRED EMBODIMENTS

The present invention provides improvements in the delivery of CPAP therapy. In particular a patient interface and cushion is described which is quieter for the patient to wear and reduces leakage from the mask, therefore providing for a good seal on a wearer's nose and face. Furthermore, the patient interface and cushion of the present invention provides for conformity to a patient's facial contours unlike other solid silicone mask or cushion designs and is comfortable for a patient to wear. Also, the cushion of the present invention is durable and allows the pressure of the face of a user to be reduced preventing face sores and the like.

It will be appreciated that the patient interface as described in the preferred embodiment of the present invention can be used in respiratory care generally or with a ventilator but will now be described below with reference to use in a humidified CPAP system. It will also be appreciated that the present invention can be applied to any form of patient interface including, but not limited to, nasal masks, oral masks and mouthpieces.

Figure 1:
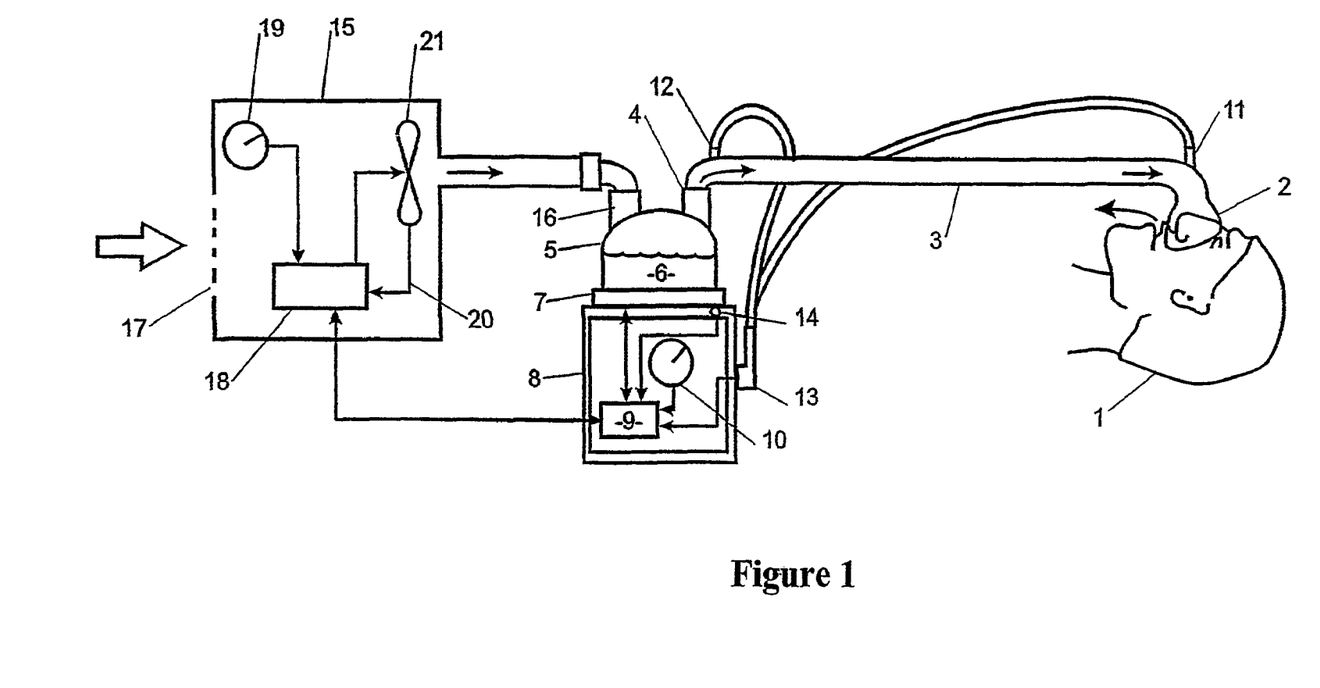
FIG. 1 is a block diagram of a humidified continuous positive airway pressure system as might be used in conjunction with the present invention.

With reference to FIG. 1 a humidified Continuous Positive Airway Pressure (CPAP) system is shown in which a patient 1 is receiving humidified and pressurised gases through a patient interface 2 connected to a humidified gases transportation pathway or inspiratory conduit 3. It should be understood that delivery systems could also be VP AP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as patient input means or dial 10 through which a patient of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the patient set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface. The water vapour is then passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 1.

Blower 15 is provided with variable pressure regulating means or variable speed fan 21 which draws air or other gases through blower inlet 17. The speed of variable speed fan 21 is controlled by electronic controller 18 (or alternatively the function of controller 18 could be carried out by controller 9) in response to inputs from controller 9 and a patient set predetermined required value (preset value) of pressure or fan speed via dial 19.

Nasal Mask

Figure 2:
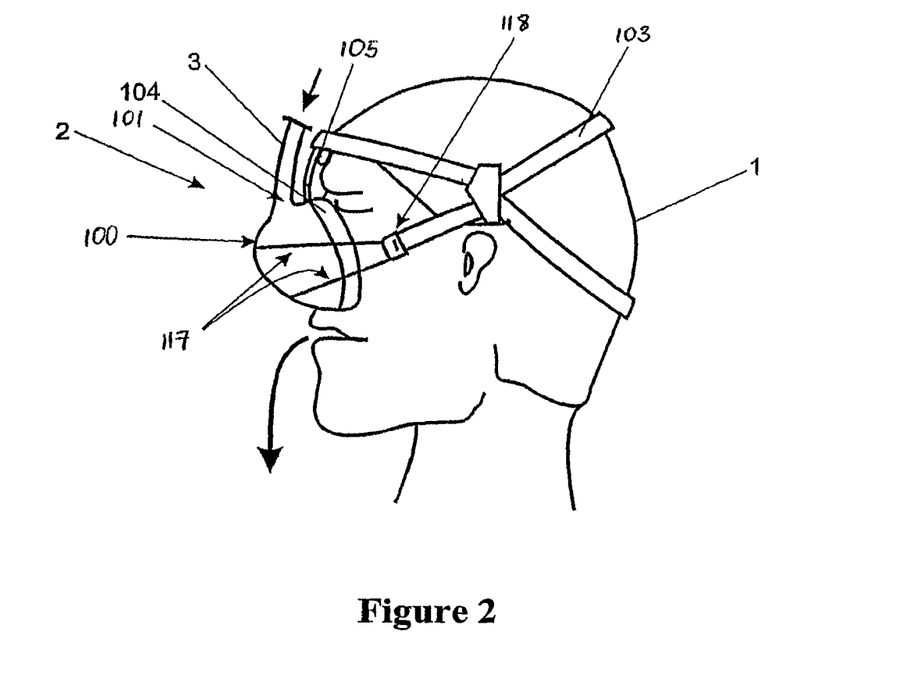
FIG. 2 is an illustration of a nasal mask in use with a cushion according to the preferred embodiment of the present invention.

According to a first embodiment of the present invention the patient interface is shown in FIG. 2 as a nasal mask. The mask includes a hollow body 100 with an inlet 101 connected to the inspiratory conduit 3. The mask 2 is positioned around the nose of the patient 1 with the headgear 103 secured around the back of the head of the patient 1. The headgear 103 preferably attaches to a gliding strap or straps 117 by way of connectors 118. The gliding straps 117 allow for the patient to move his head but the mask 2 and more particularly the cushion 104 is not pulled from the patient's face. The restraining force from the headgear 103 on the hollow body 100 and the forehead rest 105 ensures enough compressive force on the mask cushion 104, to provide an effective seal against the patient's face.

The hollow body 100 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Mask Cushion

Figure 3:
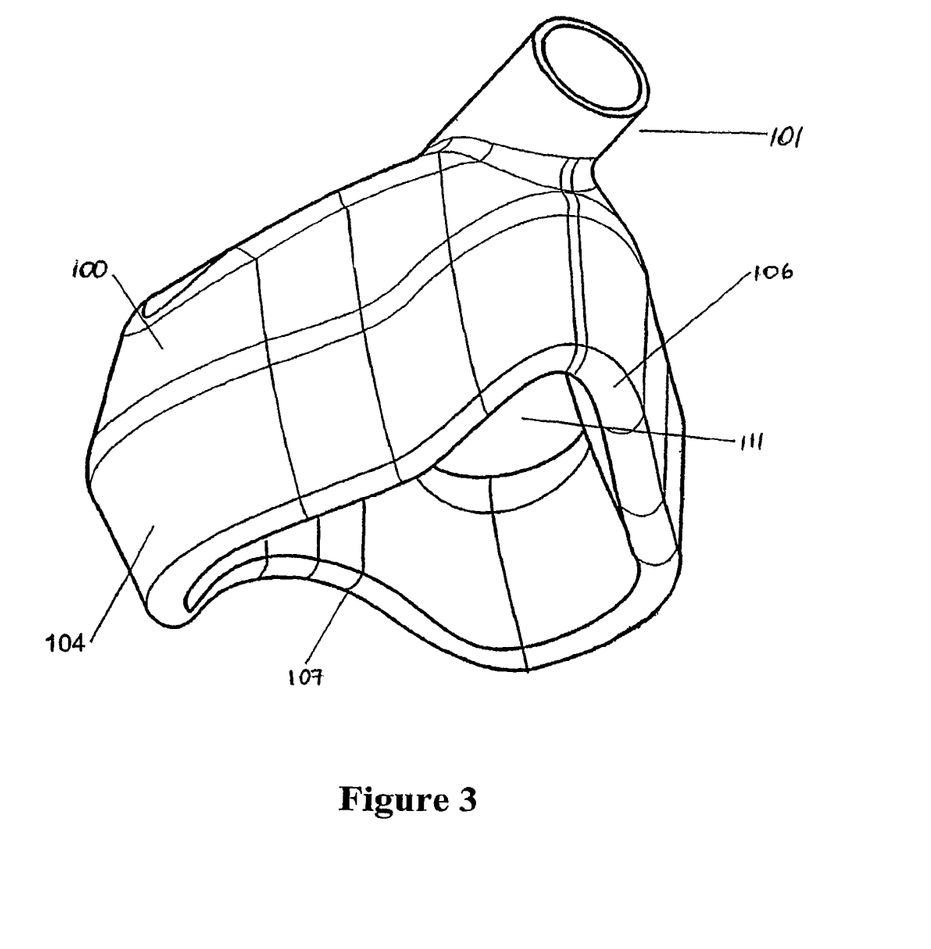
FIG. 3 shows a perspective view of the mask with cushion.
Figure 4:
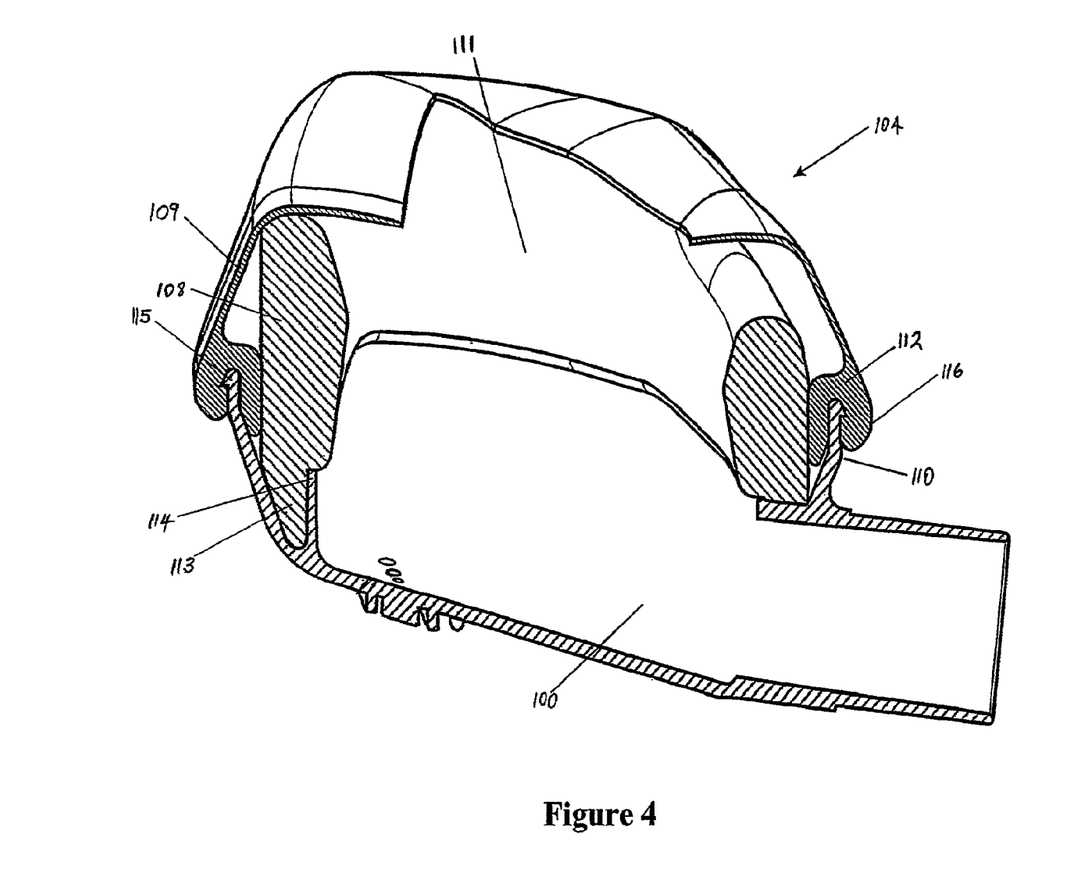
FIG. 4 is a cutaway view of the mask showing the cushion.

Referring now to FIGS. 3 and 4 in particular, the mask cushion 104 is shown in further detail. The cushion 104 is provided around the periphery of the nasal mask hollow body 100 to provide an effective seal onto the face of the patient to prevent leakage. The mask cushion 104 is shaped to approximately follow the contours of a patient's face. The mask cushion 104 will deform when pressure is applied by the headgear (108, see FIG. 2) to adapt to the individual contours of any particular patient. In particular, there is an indented section 106 that fits over the bridge of the patient's nose as well as a less indented section 107 to seal around the section beneath the nose and above the upper lip.

As shown in FIG. 4 the mask cushion 104 is composed of an inner cushion 108 covered by an outer sealing sheath 109. The inner cushion 108 is constructed of a resilient material for example, polyurethane foam, to enable distribution of pressure evenly along the seal around the patient's face. The inner cushion 108 is located around the outer periphery 110 of the open face 111 of the hollow body 100. Similarly the outer sheath 109 may be commonly attached at its base 112 to the periphery 110 and loosely covers over the top of the inner cushion 108.

In a first embodiment of the mask cushion shown in FIG. 4 the bottom of the inner cushion 108 fits into a generally triangular cavity 113 in the hollow body 100. The cavity 113 is formed from a flange 114 running mid-way around the interior of the hollow body 100. The outer sheath 109 fits in place over the cushion 108, holding it in place. The sheath 109 is secured by a snap-fit to the periphery 110 of the hollow body. The periphery 110 of the hollow body is shown including an outer bead 115. The sheath 109 includes a matching bead 116, whereby once it is stretched around the periphery 110, the two beads 115, 116 engage to hold the sheath 109 in place.

Figure 5:
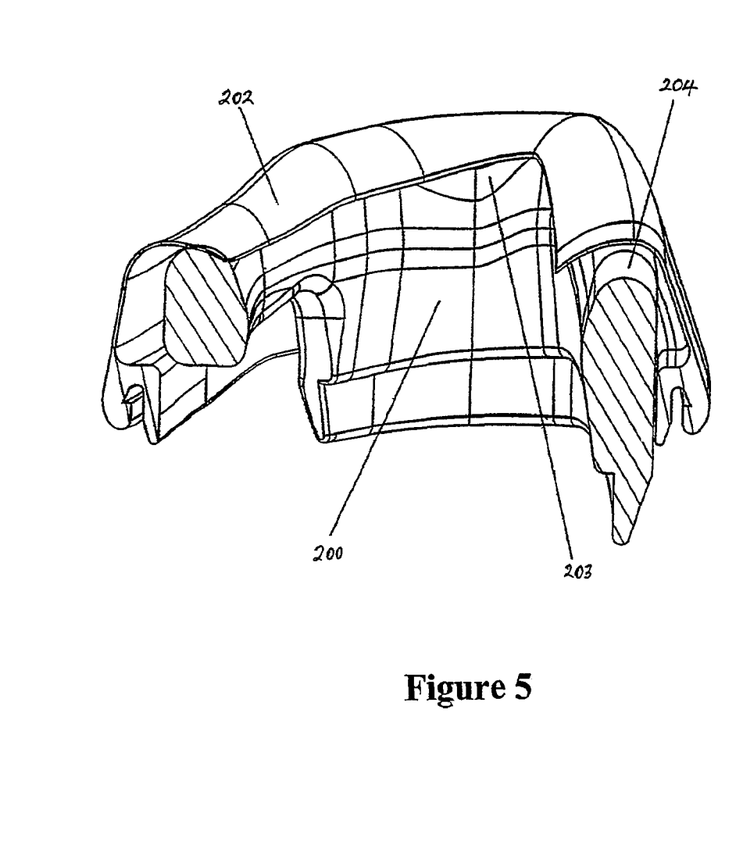
FIG. 5 shows a cross section of second preferred embodiment of the mask cushion.
Figure 6:
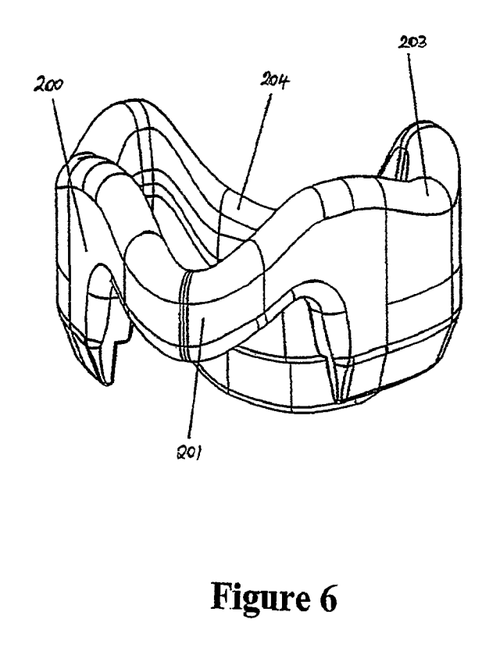
FIG. 6 shows perspective view of an inner cushion of the second preferred embodiment of the mask cushion.

Referring now to FIGS. 5 and 6, a second embodiment of the mask cushion of the present invention is depicted. In this second embodiment, the inner cushion 200 includes a raised bridge 201 in the nasal bridge region. Thus the notch in the contacting portion is less pronounced than proceeding embodiments, however as the raised bridge 201 is unsupported it is much more flexible and results in less pressure on the nasal bridge of the patient. The outer sheath 202 contacts the cushion 200 throughout the raised bridge 201.

Referring particularly to FIG. 6, the foam cushion 200 includes a check contour 203, which follows the cartilage extending from the middle of the nose, and a contoured lip sealing portion 204, to seal between the base of the nose and the upper lip.

Honeycomb Cushion

Figure 11:
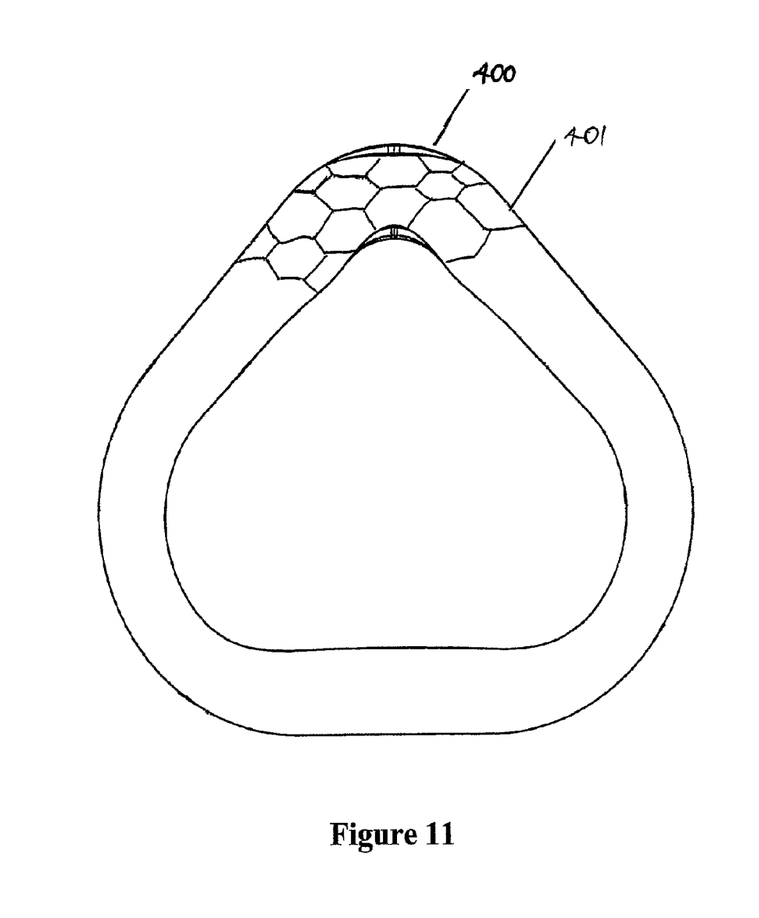
FIG. 11 shows a plan view of a mask cushion having a honeycomb-like structure.

Referring to FIG. 11, a third embodiment of the mask cushion of the present invention is illustrated. The inner cushion 400 may be formed in a honeycomb structure 401. The cushion 400 is shown in FIG. 11 with a partial area of an array of hexagonal areas or voids 401. It must be noted that select parts of the cushion could be made in the honeycomb structure, while other areas are fully formed from foam, gel, silicon, rubber or the like material. In yet other forms, the whole cushion maybe formed in this type of honeycomb-like structure.

This type of honeycomb-like structure of the cushion 400 reduces the pressure on the patient's nasal bridge region in use, meaning this cushion 400 is more comfortable to use.

The hexagonal cushion 400 is preferably formed in a silicon or rubber material and as such is likely to be more flexible, durable and hygienic. The cushion 400 is preferably formed by injection moulding in silicone. Therefore, a mould for use to mould the cushion will have hexagonal or other appropriately shaped uprights that form the voids in the cushion.

The hexagonal cushion 400 may also be coated with an outer film or coating (not shown) by similar methods as are described below. In particular, the outer coating may be formed from silicone.

Film or Coating

A reinforcement film or coating (outer cover) can be applied onto any of the above described inner cushion's outer surfaces to reduce the possibility of tearing of the inner cushion. Such a reinforcement film would likely be made of a resilient material for example polyurethane. The coating may be applied onto the cushions surface using a variety of methods, for example, injection of a foam cushion onto the pre-made film that lines the cushion mould or adhering a pre-made cushion with a plastic film using processes such as high frequency welding, ultrasonic welding, or gluing. The film or coating could be a plastic film, for example a durable polyurethane film, or a sprayed or painted on plastic or paint coating. Alternatively, the inner cushion may be dipped in a plastic or paint to coat it.

It is preferred that the mask cushion in this form be comprised of an inner cushion with an outer cover and an outer sealing sheath. Preferably the inner cushion and outer cover are formed of the same elemental material, for example, polyurethane foam and film, respectively. The outer sealing sheath is preferably made of a flexible material, such as silicone or rubber. In other forms the inner cushion may be made of a gel, silicone, or rubber like material. In this form the inner cushion is not attached to the mask but floats between the outer sealing sheath and mask body. This enables the hiller cushion, whether made from a foam or gel, silicone or rubber-like material and can be removed, enabling easy cleaning or the use of different sized inner cushions with the mask for better custom fitting for the user.

Figure 7:
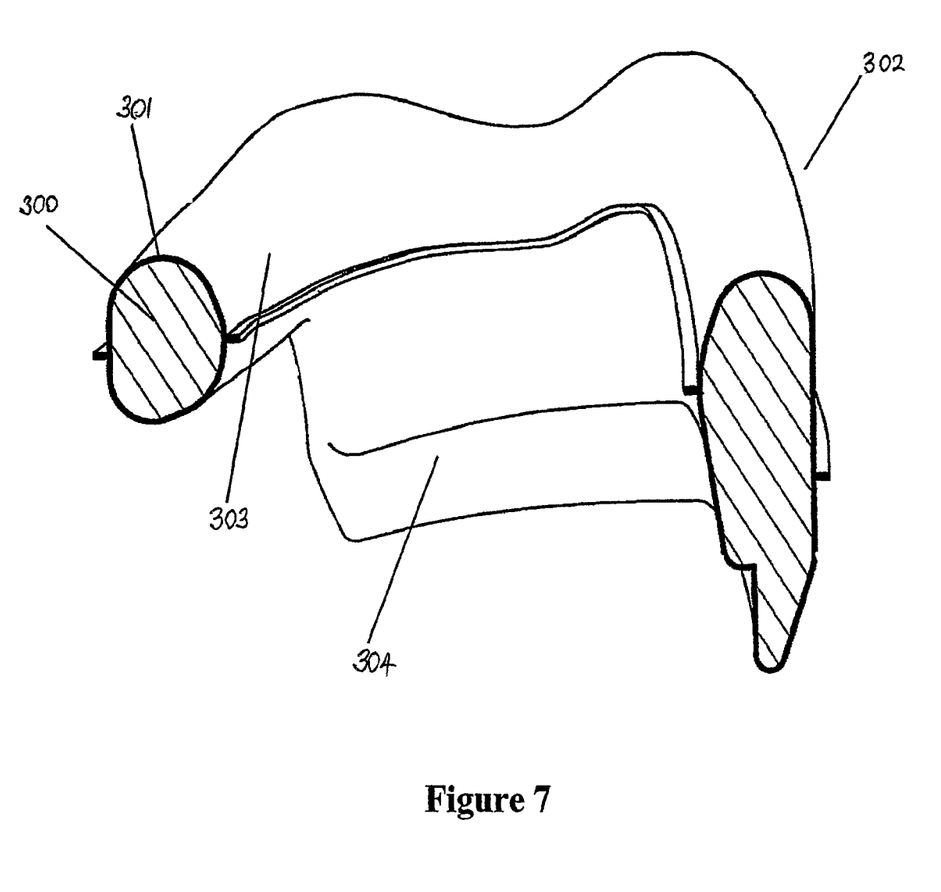
FIG. 7 shows a cross section of an inner cushion with a reinforcement film or coating.

Referring to FIG. 7, a cushion 300 with a reinforcement film 301 is illustrated as a whole cushion body 302. The cushion body 302 includes an upper outer periphery portion 303 and lower hollow fitting portion 304. The outer periphery portion 3 rests against the patient's face in use and the hollow fitting portion 304 attaches to the mask hollow body, for example, 100 in FIG. 4 in a manner as described above.

Referring to FIG. 7, the reinforcement film or coating 301 for example, a plastic film, can be applied to the outer periphery portion 303 and hollow fitting portion 304 separately, usually by injection moulding each portion, although other suitable methods such as painting or spraying may be used. Later the two portions may be joined together to form the whole cushion 300. These two portions 303, 304 can be joined using different methods; one example is by high frequency welding where high or ultrasonic frequencies cause the cushion material, for example, foam (in the preferred embodiment), to meld together. The advantage of moulding two portions and joining them to make up the cushion is that the cushion is easier to manufacture.

As an example, the two portions 303, 304 of the cushion 300 may be formed by injecting foam into female moulds, then removing these and covering them with a plastic coating then using high or ultrasonic welding to meld the two portions plastic coatings together.

In other forms the cushion 300 maybe welded on to the mask hollow body 100. In this form the cushion would be permanently attached to the mask body 100 (see FIG. 4). Here, it is likely that the mask body 100 is made from an injection moulding grade thermoplastic. A film 301 can be applied on to the pre-made portions 303, 304 or whole cushion 300 itself. For example, the reinforcement film or coating may be applied on to the pre-made cushion 300 by means of spraying (using an air-gun or the like), dipping or painting (of the mould before injecting of the cushion). Again, the cushion could be made in a single mould or in portions as described above.

In another form the film may be made of durable polyurethane and be vacuum formed onto a female mould, the mould may be a single cavity or multi-cavity to enable multiple forming of upper and lower portions of the cushion. The material making up the cushion, may then be injected into the cavity onto the film. The cushion and film are then left to cure at a temperature between 400 e and 500 e for 5 to 8 minutes. During this time the material making up the cushion (preferably foam) adheres to the film. The end result is a cushion covered with a plastic coating that will be resistant to wear, tear and moisture.

Figure 8:
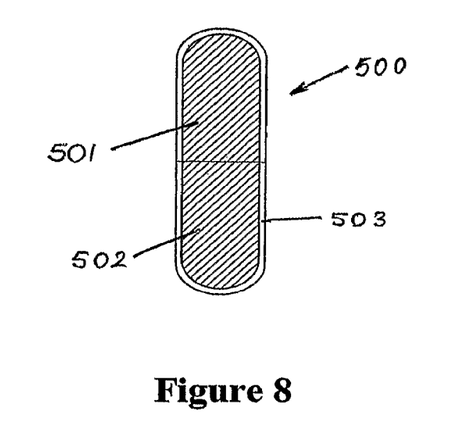
FIG. 8 shows a cross section of an inner cushion made up of two portions welded or glued in the middle.
Figure 9:
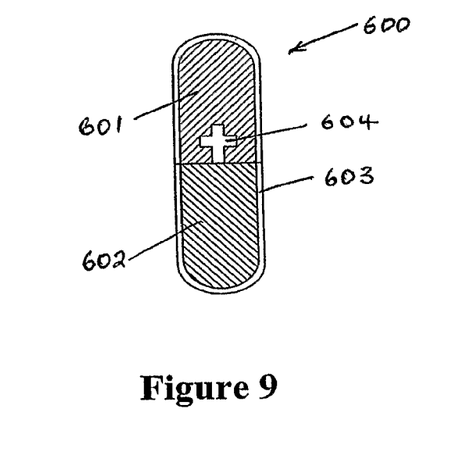
FIG. 9 shows a cross section of an inner cushion with a connecting catch between the halved portions of the cushion.

FIG. 8, shows a cross section of a cushion 500 made up of two portions 501, 502 that are each covered in a coating or film 503 (similar to those described above) that have been welded together where the portions 501, 502 meet Referring to FIG. 9, the halved portions 601, 602 of a cushion 600 maybe formed with a catch or key 604. The two parts of the catch 604 are keyed together to assist in the alignment of the portions 601, 602 and then the portions are welded together. Each of the portions 601, 602 is shown in FIG. 9 as being covered by a coating or film 603. The catch of key 604 has the purpose of assisting to align the two portions and to prevent movement of the two portions during welding.

Figure 10:
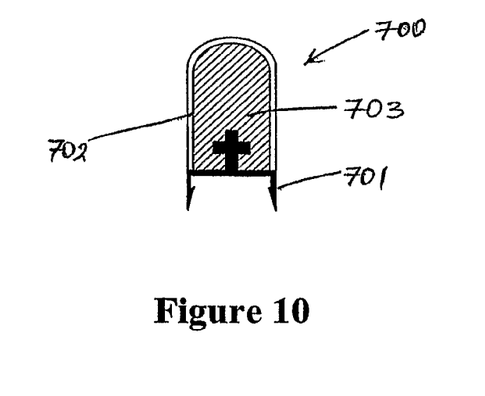
FIG. 10 shows a cross section of a halved foam cushion with mounting brackets.

Referring to FIG. 10, a cushion 700 may be attached to the mask body with a mounting bracket 701 that clips to a groove (not shown) in the hollow mask body. The cushion 703, for example, moulded of foam, is preferably directly molded on the bracket 701. The reinforcement film or coating 702 is then adhered to the cushion's surface using the methods described above, an adhesive material or high frequency or ultrasonic welding.

In alternative forms of the cushion the cushion could be moulded onto the film and then welded to the bracket. The bracket is preferably made from a polyurethane or thermoplastic and has the purpose of enabling the clipping of the cushion to the mask body.

A mask cushion with a film coating will mean that while the cushion remains flexible and soft, it is more durable. Furthermore, the cushion will be waterproof, as moisture from the patient's skin or caused by surrounding apparatus or therapy the patient is undergoing, is not absorbed by the cushion. Therefore, the cushion will also be more hygienic.

What is claimed is:

1. A cushion for a patient interface adapted to supply gas to a patient comprising:
    an inner cushion body having a cutout at a nasal region of the inner cushion body; and
    an outer sealing sheath in use adapted to engage around or adjacent the inner cushion body to retain the inner cushion body adjacent a mask hollow body, wherein the outer sealing sheath deforms substantially independently of the inner cushion body, and wherein the cutout defines a gap between the nasal region of the inner cushion body and the mask hollow body when the inner cushion body is retained adjacent the mask hollow body by the outer sealing sheath.

2. The cushion of claim 1, wherein the inner cushion body is formed of polyurethane foam.

3. The cushion of claim 1, wherein the inner cushion body is assembled from more than one molded component.

4. The cushion of claim 1, the inner cushion body having a first end adapted to be oriented towards a patient's face and a second end opposite the first end, the second end having the cutout.

5. The cushion of claim 1, wherein at least a portion of the inner cushion body comprises a plurality of adjacent voids.

6. The cushion of claim 5, wherein each of the voids has a hexagonal cross section.

7. The cushion of claim 5, wherein each of the voids has an oval, square, rectangular, or other shaped cross section.

8. The cushion of claim 5, wherein the voids form a honeycomb structure within the cushion body.

9. The cushion of claim 1, wherein a honeycomb structure is present in a part of the cushion that contacts a nasal bridge of a patient when in use to reduce the pressure on the patient's nasal bridge.

10. The cushion of claim 1, wherein the inner cushion body further comprises a cheek contour shaped to follow the cartilage extending from the middle of a patient's nose.

11. The cushion of claim 1, wherein, when the outer sealing sheath is engaged around or adjacent the inner cushion body, the outer sealing sheath remains in contact with the inner cushion body at the nasal region of the inner cushion body.

12. A mask adapted to supply gas to a patient comprising:
    a hollow body; and
    a cushion provided around a periphery of the hollow body, the cushion comprising:
        an inner cushion having a cutout at a nasal region of the inner cushion; and
        an outer sealing sheath adapted to seal on the patient's face in use, wherein the outer sealing sheath deforms substantially independently of the inner cushion body, and wherein the cutout defines a gap between the nasal region of the inner cushion body and the mask hollow body when the inner cushion is retained adjacent the mask hollow body by the outer sealing sheath.

13. The cushion of claim 12, wherein at least a portion of the inner cushion comprises a honeycomb structure.

14. The cushion of claim 12, wherein at least a portion of the inner cushion is made of silicone.

15. The cushion of claim 12, wherein at least a portion of the inner cushion is made of polyurethane foam.

16. The cushion of claim 12, wherein an outer cover or film is applied on to or adhered to outer surfaces of the inner cushion, the outer cover or film reinforcing the inner cushion to reduce the possibility of tearing of the inner cushion.

* * * * *